United States Patent [19]
Blenke et al.

[11] Patent Number: 6,020,535
[45] Date of Patent: Feb. 1, 2000

[54] EXTENSIBLE ABSORBENT ARTICLE INCLUDING A RELEASE AGENT

[75] Inventors: Timothy James Blenke, Neenah; Jennifer Elizabeth Pozniak, Appleton; Dale Alan Burghardt, Butte Des Morts, all of Wis.

[73] Assignee: Kimberly-Clark Worldwide, Inc., Neenah, Wis.

[21] Appl. No.: 09/002,279

[22] Filed: Dec. 31, 1997

[51] Int. Cl.$^7$ ...................................................... A61F 13/15
[52] U.S. Cl. ........................ 604/367; 604/358; 604/365; 604/385.1; 604/385.2
[58] Field of Search .................................... 604/391, 369, 604/385.2, 373, 368, 378, 367, 358, 365, 385.1

[56] References Cited

U.S. PATENT DOCUMENTS

| | | | |
|---|---|---|---|
| 4,194,507 | 3/1980 | Ness et al. ................................ | 128/287 |
| 4,353,762 | 10/1982 | Bouda ...................................... | 156/164 |
| 4,534,769 | 8/1985 | DeJonckheere et al. ................ | 604/369 |
| 4,547,243 | 10/1985 | Brody ....................................... | 156/164 |
| 4,568,344 | 2/1986 | Suzuki et al. ............................ | 604/389 |
| 4,573,987 | 3/1986 | Lamb, Jr. ................................. | 604/378 |
| 4,634,482 | 1/1987 | Lammers ................................. | 156/164 |
| 4,701,171 | 10/1987 | Boland et al. ........................... | 604/385 A |
| 4,701,173 | 10/1987 | Zehner et al. ........................... | 604/385 A |
| 4,747,846 | 5/1988 | Boland et al. ........................... | 604/38 A |
| 4,770,656 | 9/1988 | Proxmire et al. ........................ | 604/393 |
| 4,808,176 | 2/1989 | Kielpikowski ........................... | 604/385.2 |
| 4,834,736 | 5/1989 | Boland et al. ........................... | 604/385.2 |
| 4,834,738 | 5/1989 | Kielpikowski et al. ................. | 604/385.2 |
| 4,850,990 | 7/1989 | Huntoon et al. ......................... | 604/385.2 |
| 4,872,871 | 10/1989 | Proxmiro et al. ........................ | 604/394 |
| 4,892,598 | 1/1990 | Stevens et al. .......................... | 156/91 |
| 4,994,054 | 2/1991 | Pigneul et al. .......................... | 604/391 |
| 5,226,992 | 7/1993 | Morman ................................... | 156/62.4 |
| 5,593,400 | 1/1997 | O'Leary ................................... | 604/385.2 |
| 5,611,790 | 3/1997 | Osborn, III et al. .................... | 604/391 |
| 5,702,378 | 12/1997 | Widlund et al. ......................... | 604/373 |
| 5,800,419 | 9/1998 | Soga et al. ............................... | 604/368 |
| 5,824,004 | 10/1998 | Osborn, III et al. .................... | 604/385.2 |
| 5,827,259 | 10/1998 | Laux et al. .............................. | 604/385.2 |
| 5,833,677 | 11/1998 | Sauer ....................................... | 604/369 |
| 5,843,056 | 12/1998 | Good et al. .............................. | 604/367 |

*Primary Examiner*—John G. Weiss
*Assistant Examiner*—Miley Craig Peppers, III
*Attorney, Agent, or Firm*—Jerry F. Janssen; Brian R. Tumm

[57] ABSTRACT

An absorbent article includes an absorbent pad and an outer cover. A release agent is applied to one of the outer surface of the absorbent pad and the inner surface of the outer cover. The release agent prevents at least a portion of the outer cover from adhering to the absorbent pad. In embodiments where the outer cover is extensible in a cross-direction and/or a longitudinal direction, the release agent prevents the absorbent pad from resisting mobility of the outer cover. Thus the absorbent pad has substantially no adhesion to the outer cover where the release agent is applied. Therefore, tearing of the absorbent pad and damage to, or release, of superabsorbent material from the absorbent pad during extension of the outer cover, is prevented. The release agent can be a silicon-active agent or a powder material having properties that prevent adhesion between adhesive and a forming tissue of the absorbent pad, or the outer cover.

49 Claims, 3 Drawing Sheets

EXTENSIBLE ABSORBENT ARTICLE INCLUDING A RELEASE AGENT

CROSS REFERENCE TO RELATED APPLICATIONS

Not Applicable

STATEMENT REGARDING FEDERALLY SPONSORED RESEARCH OR DEVELOPMENT

Not Applicable

FIELD OF THE INVENTION

Absorbent articles such as infant diapers, training pants, adult incontinence products, and the like are well known. Such absorbent articles have achieved wide acceptance due to their ability to receive and absorb body exudates, whether large amounts or small, and generally include an absorbent core therein.

In typical absorbent articles, an absorbent pad has an absorbent core contained within a barrier tissue and a forming tissue. The absorbent pad is located between an outer cover and a bodyside liner.

This invention pertains to extensible absorbent articles for use in storing exudates. The outer cover generally comprises a material extensible in at least one direction. An adhesive is generally applied to a first inner surface of the outer cover. A release agent is applied to a first outwardly facing surface of the forming tissue or a portion of the inner surface of the outer cover over the adhesive. The release agent prevents the forming tissue, over the effective area, from securing to the outer cover. Thus the absorbent pad is not adhered to the extensible outer cover, over the effective area, between the bodyside liner and the outer cover. Therefore, the absorbent pad does not tear when the absorbent article is extended in at least the direction in which the outer cover is extensible.

BACKGROUND OF THE INVENTION

In general, absorbent articles should comfortably fit the body of a wearer. Most absorbent articles include an absorbent pad formed by an absorbent core contained in a wrap comprising a barrier tissue and/or a forming tissue. The subject invention discloses an absorbent article and a method of making an absorbent article generally having extensibility in at least one direction, preferably the cross-direction. Such extensibility permits an absorbent article to extend and expand about and conform to the body of the wearer. Such extension and expansion about the wearer is feasible because both the bodyside liner and the outer cover are extensible in at least the one direction.

However, in conventional structures, the outer cover is typically adhesively secured to the forming tissue of the absorbent pad. In such embodiments, extending the outer cover in the cross-direction extends the absorbent pad in the cross-direction. In such embodiments, the force used to extend the outer cover, and thence the absorbent pad, can tear or otherwise damage the absorbent pad. Since the absorbent pad is typically a sealed enclosure, namely an absorbent core enclosed within the combination of a forming tissue and a barrier tissue, tearing the absorbent pad, namely either the forming tissue or the barrier tissue, can release superabsorbent particles and other materials into contact with the body of the wearer. The particles can irritate the skin of the wearer, and indicate failure of the absorbent article to perform properly. Therefore, it is critical, and essential, to find a way to prevent tearing or other structural failure of the absorbent pad.

SUMMARY OF THE DISCLOSURE

In the present invention, an absorbent article includes an absorbent pad having a first surface and an opposing second surface, an outer cover having a third surface and a fourth surface, a pattern of adhesive material disposed on the first surface of the absorbent pad or on the third surface of the outer cover, and an effective amount of a release agent disposed on one of the first surface of the absorbent pad and at least a portion of the third surface of the outer cover, the release agent preventing adhesion of the third surface of the outer cover to the first surface of the absorbent pad such that an absorbent core disposed in the absorbent pad has substantially no adhesion to the outer cover over the surface effectively treated with the release agent.

In some embodiments, the absorbent pad includes a first tissue disposed in surface-to-surface relationship with the first surface of said absorbent core, such that the release agent is applied to one of the first tissue of the absorbent pad and at least a portion of the third surface of said outer cover.

In most embodiments, the absorbent article includes a bodyside liner, and a second tissue disposed between the bodyside liner and the absorbent core. The second tissue and first tissue are preferably secured to each other about at least a portion of an outer perimeter of the absorbent core to thereby enclose the absorbent core.

In some embodiments, at least one of the bodyside liner and the outer cover comprise resiliently extensible material. In some embodiments, bodyside liner and outer cover are both resiliently extensible, and may have substantially the same amounts of extensibility, each as the other, in a given direction.

In some embodiments, the outer cover comprises a necked bonded laminate.

In some embodiments, the bodyside liner and the outer cover are both extensible in at least the cross-direction.

In some embodiments, the absorbent article includes a surge layer disposed between the bodyside liner and the second tissue. The surge layer can be secured to the bodyside liner by hot melt adhesive.

In some embodiments, the absorbent article includes first and second containment flaps.

In some embodiments, the release agent comprises a silicone-active material disposed on one of the first tissue and the outer cover. The silicone-active material can comprise an amino functional silicone.

In other embodiments, the release agent comprises a powder material applied to one of the first tissue and the outer cover. The powder material can comprise, for example, corn starch, erucamide, baking soda, talc, or calcium sterate, among other materials.

In preferred embodiments, the adhesive material secures the outer cover to the bodyside liner at locations disposed outwardly of an outer perimeter of the absorbent pad.

In some embodiments, the absorbent article is free from waist elastic elements.

In some embodiments, the absorbent article includes leg elastics disposed at least in the crotch portion to provide extensibility and retraction in a longitudinal direction.

In some embodiments of the invention, the absorbent article comprises a bodyside liner having a body contacting surface and an opposing surface, the opposing surface being mounted in surface-to-surface relationship to at least a portion of the outer cover, the outer cover including adhesive material on an inner surface thereof, a release agent interacting with the adhesive material and thereby preventing, over the surface effectively treated with the release agent, adhesion of the outer cover to the first tissue.

In preferred embodiments, the release agent permits extension of the outer cover in the cross-direction without damage to the absorbent pad.

In preferred embodiments, the bodyside liner comprises an extensible material.

In some embodiments, the bodyside liner and outer cover are both extensible in at least the cross-direction, the release agent enabling the outer cover to extend at least about 30 percent, and preferably at least about 200 percent, in the cross-direction without damaging the absorbent pad. Further, the release agent can enable the outer cover to extend at least about 30 percent in the longitudinal direction without damaging the absorbent pad.

In some embodiments, the first tissue defines a contact area in general surface-to-surface relationship with a surface of the outer cover, the silicone-active agent acting as a coating distributed over substantially the entirety of the contact area of the first tissue.

In many embodiments, the absorbent pad is unattached to either of the bodyside liner or outer cover.

An embodiment for a method of making an absorbent article includes the steps of: applying a release agent to a first outer surface of a first tissue, the first tissue, in combination with a second tissue, substantially enclosing an absorbent core to thereby form an absorbent pad; applying adhesive to a second inner surface of an extensible outer cover; and placing at least a first portion of the first surface of the first tissue of the absorbent pad in surface-to-surface relationship with at least a second portion of the second surface of the outer cover such that the outer cover, including a portion of the adhesive, interacts with the release agent, whereby, over the surface effectively treated with the release agent, the release agent prevents the adhesive from adhering the outer cover to the absorbent pad, and thus permits resilient extension of the outer cover in at least one direction without damage to the absorbent pad. The adhesive can be a hot melt adhesive sprayed onto the outer cover.

In some embodiments, the method includes the step of applying a bodyside liner to the second tissue such that the bodyside liner overlies, and extends outwardly of, the absorbent pad, and overlies and contacts portions of the outer cover which extend outwardly of the absorbent pad, including the bodyside liner contacting at least part of the adhesive on the outer cover which is disposed outwardly from the outer perimeter of the absorbent pad.

In some embodiments, the method includes applying a longitudinally-extending line of hot melt adhesive to a first surface of a surge layer, and adhesively securing the surge layer to the bodyside liner such that the surge layer is located between the bodyside liner and the absorbent pad.

In some embodiments, the method includes applying cold adhesive to secure the first tissue to the second tissue about substantially an entire perimeter of facing portions of the first tissue and the second tissue such that the combination of the first tissue and the second tissue provides a closed enclosure within which the absorbent core is received and retained.

In some embodiments, the step of applying the release agent comprises applying, onto one of the first tissue and the outer cover, an amount of silicone-active agent effective to prevent the adhesive on the outer cover from adhering to the first tissue.

In other embodiments, the step of applying the release agent comprises applying, onto at least one of the first tissue and outer cover, an amount of powder material, for example corn starch or talc, effective to prevent the adhesive on the outer cover from adhering to the first tissue.

In some embodiments, the release agent can be pre-applied to the first tissue before starting the manufacturing process for the absorbent article.

Figure 1:
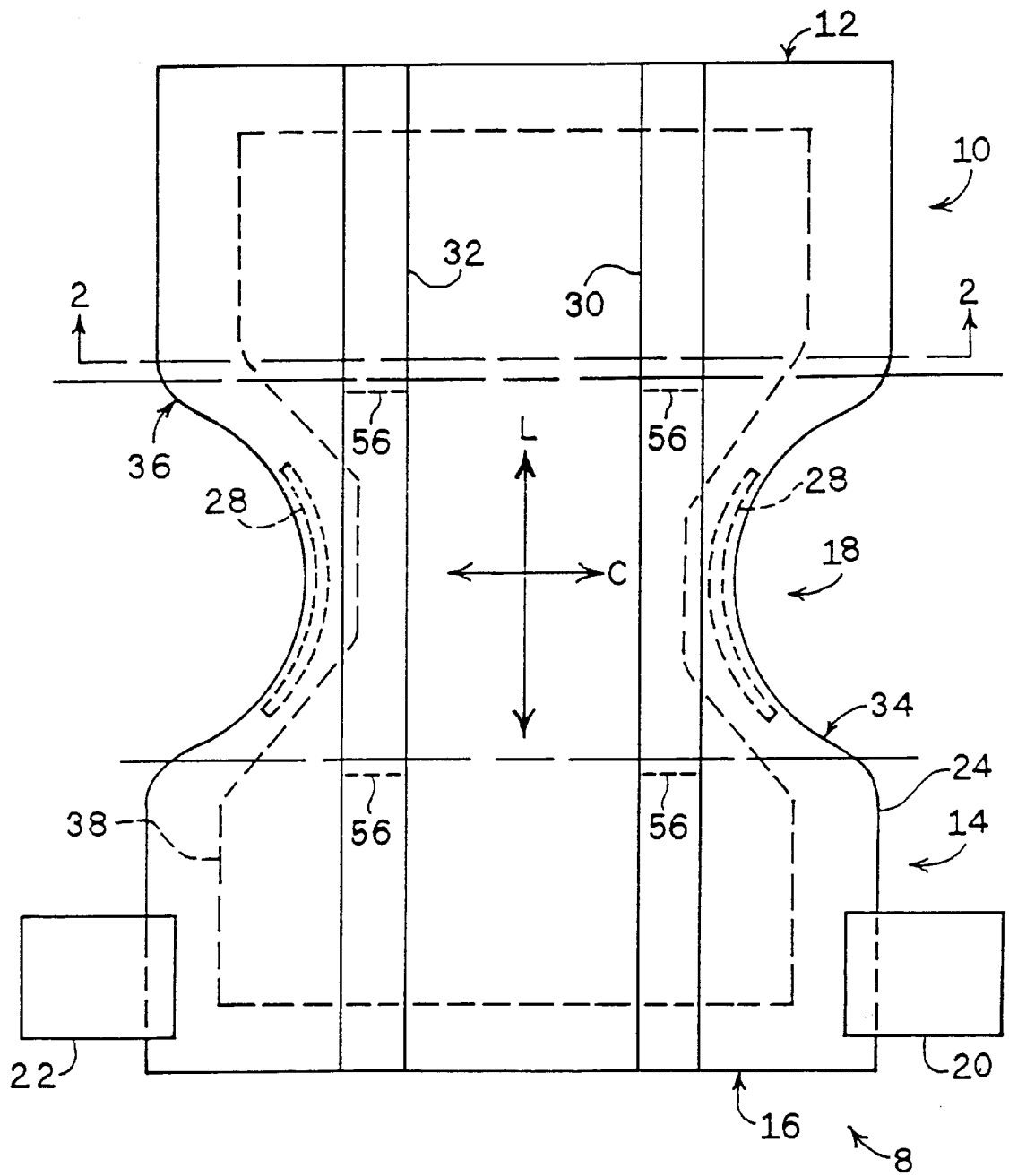
FIG. 1 shows a top view of a first embodiment of absorbent articles of the invention.

The invention is not limited in its application to the details of the construction and the arrangement of the components set forth in the following description or illustrated in the drawings. The invention is capable of other embodiments or of being practiced or carried out in various ways. Also, it is to be understood that the terminology and phraseology employed herein is for purpose of description and illustration and should not be regarded as limiting. Like reference numerals are used to indicate like components. The drawings are for purposes of illustration, and are not necessarily drawn to scale.

DETAILED DESCRIPTION OF THE ILLUSTRATED EMBODIMENTS

The various embodiments of the present invention will be described in relationship to their use in absorbent articles, but it should be understood that potential uses of the structures of the present invention need not be limited to the context of absorbent articles.

As used herein and in the claims that follow, the phrase "absorbent article" is meant to include diapers, training pants, adult incontinence articles, feminine hygiene products, and the like. Such articles generally receive and/or store urine and/or fecal material, or have a significant other absorbent function.

FIG. 1 is a representative plan view of an absorbent article 8 at one embodiment of the present invention, in its uncontracted state (i.e. with all elastic induced gathering and contraction removed). Absorbent article 8, shown in FIG. 1, includes a front portion 10 having a front edge 12, a rear portion 14 having a rear edge 16, and a crotch portion 18 between front portion 10 and rear portion 14. Fastening tabs 20, 22 are secured to bodyside liner 24 at opposing sides of rear portion 14 of absorbent article 8. Fastening tabs 20, 22 extend outwardly from the sides of rear portion 14. Outer cover 26 (shown in FIG. 2) lies in surface-to-surface relationship with bodyside liner 24. Leg elastics 28 provide generally longitudinal retractable extensibility and support in crotch portion 18. Containment flaps 30, 32 extend longitudinally along the length of absorbent article 8 inwardly of respective side edges 34, 36 of the absorbent article. Containment flaps 30, 32 are typically secured to bodyside liner 24. Absorbent pad 38 may have an hour-glass shape and is disposed between bodyside liner and outer cover.

Figure 2:
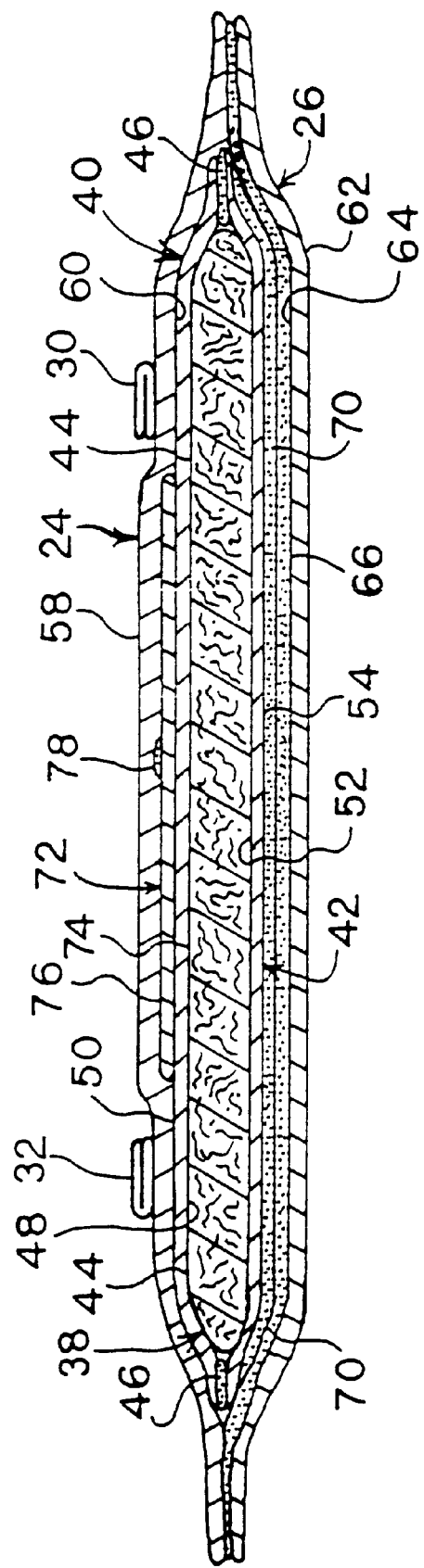
FIG. 2 shows a cross section of the absorbent article taken at line 2—2 of FIG. 1.

FIG. 2 illustrates a cross-section view taken at 2—2 of FIG. 1. Absorbent pad 38 is located between bodyside liner 24 and outer cover 26. Absorbent pad 38 includes a barrier tissue 40 and a forming tissue 42 surrounding an absorbent core 44. An adhesive 46 secures barrier tissue 40 and forming tissue 42 to each other. Thus barrier tissue 40 and forming tissue 42 envelope absorbent core 44 and form absorbent pad 38. Barrier tissue 40 includes a first surface 48 and a second opposing surface 50. Likewise, forming tissue 42 includes a first inner surface 52 and a second opposing outer surface 54. Absorbent pad 38 receives and retains exudates that pass through bodyside liner 24. Adhesive 46 secures first surface 48 of barrier tissue 40 to first surface 48 of forming tissue 42 about an outer perimeter of absorbent core 44.

Bodyside liner 24 has a first surface 58 and a second opposing surface 60. Outer cover 26 includes a first outer surface 62 and a second opposing inner surface 64. A layer of adhesive 66 is disposed on second inner surface 64 and secures outer cover 26 to bodyside liner 24.

In the preferred embodiments of the invention, outer cover 26 and bodyside liner 24 are extensible, preferably resiliently extensible, elements. Outer cover 26 preferably is extensible at least in cross-direction "C". In such an arrangement, extension of outer cover 26, if firmly secured to absorbent pad 38 at first forming tissue 42, could apply force to the absorbent pad causing the forming tissue and/or barrier tissue 40 to tear and thus allowing superabsorbent material to escape. Such a problem could cause discomfort to a user and would be considered product failure. Therefore, the invention generally prevents adhesive layer 66 from securing outer cover 26 to forming tissue 42 over a desired area of the interface between outer cover 26 and forming tissue 42. This objective is achieved by applying an effective amount of release agent 70 onto either or both of the forming tissue 42 and the adhesive layer 66. An effective amount of release agent 70 prevents adhesion/securing of adhesive layer 66 to forming tissue 42. Thus release agent 70 provides absorbent pad 38 with substantially no adhesion to outer cover 26 over that portion of the surface effectively treated with the release agent.

In other embodiments, release agent 70 can be applied such that a narrow portion of adhesive layer 66 at the center of absorbent pad 38 and extending in longitudinal direction "L" does not receive any of the release agent. Therefore, outer cover 26 can be secured to absorbent pad 38 in a manner similar to the securement shown by adhesive line 78 in FIG. 2 securing surge layer 72 to bodyside liner 24. Such an arrangement prevents absorbent pad 38 from moving away from a centered position in absorbent article 8 and permits extension of outer cover 26 in cross-direction "C" without stretching or tearing the absorbent pad.

Release agent 70 is shown, for purposes of illustration, as a layer of material located between forming tissue 42 and adhesive layer 66 of outer cover 26. However, release agent 70 can comprise a coating or other layer of material applied to second outer surface 54 of forming tissue 42 before absorbent pad 38 is placed on adhesive 66, or a coating or other layer of material applied to outer cover 26 over portions of adhesive layer 66.

FIG. 2 also illustrates surge layer 72 having a first surface 74 and a second surface 76. First surge layer surface 74 is disposed in surface-to-surface relationship with second surface 50 of barrier tissue 40. Since no adhesive is directly applied between bodyside liner 24 and absorbent pad 38, the absorbent pad has relatively free mobility with respect to bodyside liner 24.

A line of adhesive 78 located in the longitudinal direction "L" extends along the center of bodyside liner 24. Adhesive 78 thus secures bodyside liner 24 to second surface 76 of surge layer 72 along a longitudinal centerline, thereby securing surge layer 72 at a proper location to bodyside liner 24 for use in absorbent article 8. Having a longitudinal line of adhesive 78 allows bodyside liner 24 freedom to extend outwardly in the cross-direction "C" without significant resistance from surge layer 72 whereby the integrity of the surge layer is typically not threatened by such extension.

Line of adhesive 78 between surge layer 72 and bodyside liner 24 provides securement of the surge layer to the bodyside liner. Adhesive 78 preferably comprises a hot melt adhesive extending in longitudinal direction "L" along the center of surge layer 72, as illustrated in FIG. 2. Thus surge layer 72 is secured to bodyside liner 24 and generally permits relatively free movement of absorbent pad 38 with respect to the surge layer.

Fastening tabs 20, 22 can comprise hook and loop fasteners for securing rear portion 14 of absorbent article 8 to front portion 10. Other well known securing elements can be used to support absorbent article 8 on the user. For example, a cohesive system, an adhesive fastener system, or the like may be utilized as securing elements, with suitable cooperating elements on front portion 10, as necessary, to support absorbent article 8 on the wearer. One example of a fastening tab is shown in U.S. patent application Ser. No. 421,640 filed Apr. 13, 1995 by Zehner et al, titled "Multi-Attachment Fastening System" the disclosure of which is hereby incorporated by reference in its entirety, to the extent such disclosure is consistent (not contradictory) with the subject matter disclosed herein.

Fastening tabs 20, 22 can be permanently secured to rear portion 14 of absorbent article 8 by, for example, ultrasonic bonding, adhesives, stitching, or other conventional and known methods of securement.

Figure 3:
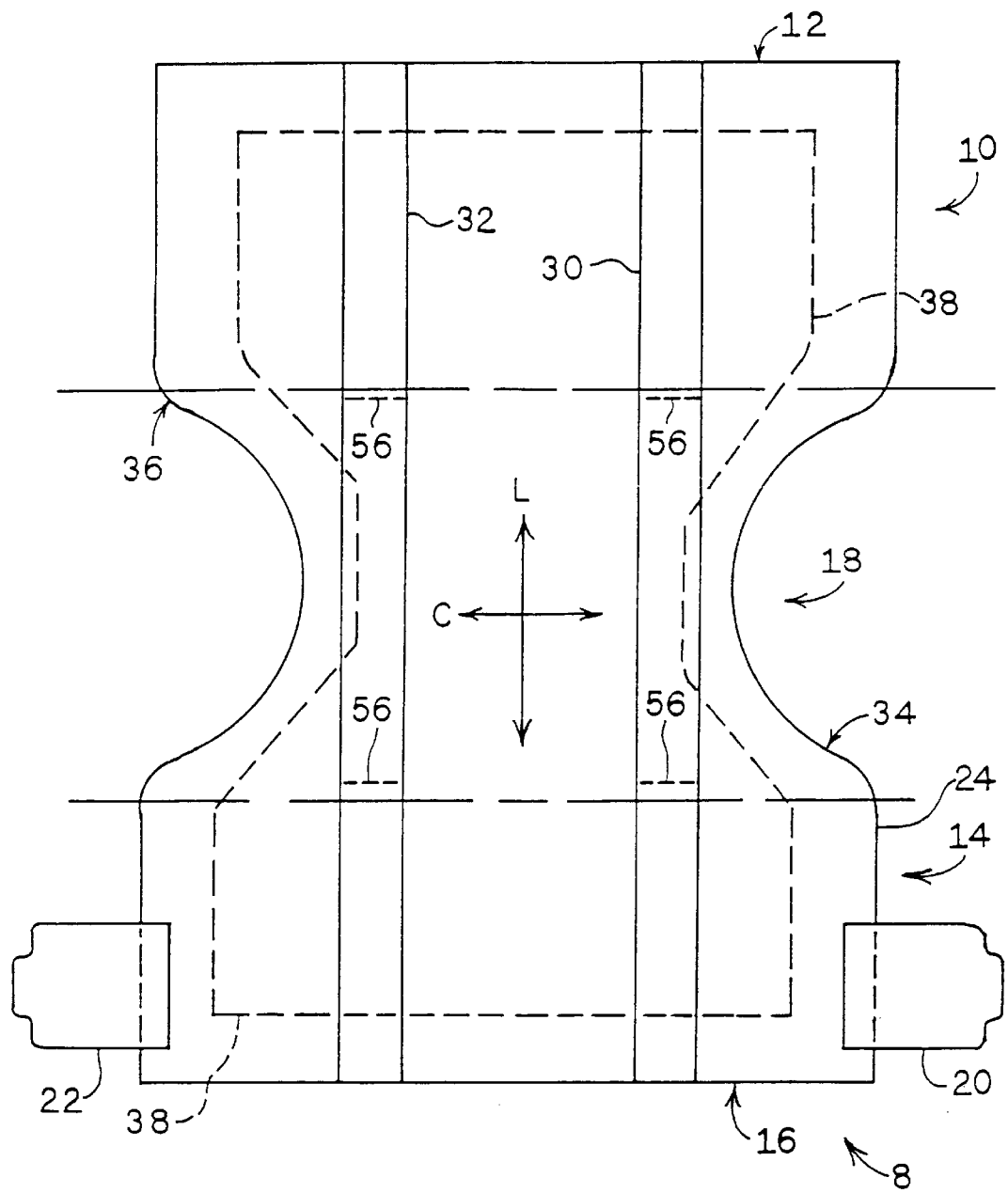
FIG. 3 shows a second embodiment having no leg elastics.

As representatively shown in FIGS. 1 and 3, bodyside liner 24 and outer cover 26 generally are coextensive and have length and width dimensions larger than the dimensions of absorbent pad 38. Thus bodyside liner 24 is generally superimposed over the entirety of the surface of outer cover 26, thereby defining the periphery of absorbent article 8. Absorbent pad 38 is preferably disposed between outer cover 26 and bodyside liner 24 inboard of the periphery of absorbent article 8.

Bodyside liner 24 includes first skin-facing surface 58 which is compliant, soft-feeling, and non-irritating to the wearer's skin. Further, bodyside liner 24 must be sufficiently porous to be permeable to aqueous liquids, permitting such liquid to penetrate and pass through its thickness.

A suitable bodyside liner 24 may be manufactured from a wide selection of web materials, such as porous foams, reticulated foams, apertured plastic films, woven and/or nonwoven natural fibers, synthetic fibers, or a combination of natural and synthetic fibers. Bodyside liner 24 is typically employed to help isolate the wearer's skin from liquids held in absorbent pad 38. Various woven and nonwoven fabrics can be used for bodyside liner 24. For example, bodyside liner 24 may be composed of a meltblown or spunbonded web of polyolefin fibers. Bodyside liner 24 may also be a bonded-carded-web composed of natural and/or synthetic fibers.

Bodyside liner 24 may be composed of a substantially hydrophobic and substantially nonwettable material, with the hydrophobic material optionally being treated with a surfactant or otherwise processed to impart a desired level of wettability and hydrophilicity.

In a preferred embodiment of the invention, bodyside liner 24 has extensibility, preferably resilient extensibility, in at least one direction. "Resiliently extensible" can be defined as a material that is retractable to substantially its original length or width upon release of an extending force. For example, bodyside liner 24 can be a nonwoven, spunbonded polypropylene fabric. See U.S. Pat. No. 5,226,992 to Morman et al. hereby incorporated by reference in its entirety, to the extent it is consistent with the disclosure herein, for teaching various materials which can be used in forming bodyside liner 24. The fabric can be creped or necked such that it is extensible in at least one of, or both of, the "L" and "C" directions (in the longitudinal direction "L" and/or the cross direction "C").

Bodyside liner 24 may comprise a multiplicity of components, layers, or partial layers, which correspond to any of the materials disclosed herein, as well as others known in the art. The fabric can be treated with a selected amount of surfactant, such as about 0.28% Trition X-102 surfactant available from Rohm and Haas Corp. of Philadelphia, Pa. The surfactant can be applied by any conventional means such as spraying, printing, brush coating or the like.

In yet another embodiment of the present invention, bodyside liner 24 can comprise a stretch-bonded laminate having appropriate elasticity and width to create overall surface contact between absorbent article 8 and the body of a user. A stretch-bonded laminate comprises at least a two-layered composite in which one layer is a gatherable layer and the other layer a stretchable layer. The layers are joined together when the stretchable layer is in a stretched condition so that, upon relaxing the composite of the joined layers, the gatherable layer is gathered. The stretchable layer can be a film of stretchable material, such as a layer of styrene ethylene butylene styrene copolymer or other elastomeric polymer, or a plurality of optionally spaced strands of a stretchable material such as latex. Other materials with similar properties may also be provided integral with or attached to bodyside liner 24. Such materials should not interfere with the soft texture of bodyside liner 24 against the skin of a user.

Bodyside liner 24 preferably has an extensibility of at least about 30%, more preferably at least about 200%, in the cross-direction "C". In some embodiments, bodyside liner 24 additionally can have similar extensibility in longitudinal direction "L". In other embodiments, bodyside liner 24 can be extensible only in longitudinal direction "L".

Outer cover 26 preferably comprises a first material extending over and about substantially the entirety of the overall area of the absorbent article 8, and capable of being extended in at least the cross-direction "C". Such materials include knitted and loosely woven fabrics, bonded carded webs, spunbonded webs and meltblown webs. A meltblown web typically includes meltblown microfibers. The material may also have multiple layers such as, for example, multiple spunbonded layers and/or meltblown layers. The material may be made of polymers such as, for example, polyolefins. Exemplary polyolefins include polypropylene, polyethylene, ethylene copolymers and propylene copolymers. See U.S. Pat. No. 5,226,992 to Morman et al., hereby incorporated by reference in its entirety to the extent it is consistent (not contradictory) herewith, for teaching various materials which can be used to form outer cover 26. A preferred material for the outer cover layer 26 can comprise an extensible film laminated to a necked nonwoven spunbonded material.

Alternative constructions of outer cover 26 may include a woven or non-woven fibrous web layer which has been totally or partially constructed or treated to impart the desired levels of liquid impermeability to selected regions thereof, such as regions that are adjacent or proximate absorbent pad 38. Optionally, in some embodiments, an additional outer cover layer may overlay outer cover 26.

Outer cover 26 may optionally be composed of microporous, breathable material that permits vapors to escape from the absorbent article while preventing liquid exudates from passing through. For example, a suitable microporous film is a material known as PMP-1, which is available from Mitsui Toatsu Chemicals, Inc. a company having offices in Tokyo, Japan; or polyolefin film known as XKO-8044 and available from 3M Company of Minneapolis. Minn.

In another embodiment of the invention, outer cover 26 can be a nonwoven, spunbond polypropylene fabric. The fabric can be creped or necked such that it is extensible in at least one of the "L" and "C" directions or in both the longitudinal direction and the cross direction "C". Outer cover 26 can have an extensibility of at least about 30% and preferably at least about 200% in the cross-direction "C". In some embodiments, outer cover 26 additionally can have similar extensibility in longitudinal direction "L".

Other materials having other advantageous characteristics are also useful as outer cover 26. For example, outer cover 26 can comprise a stretch-bonded laminate. Methods of making such materials are known to those skilled in the art.

Preferably both bodyside liner 24 and outer cover 26 are extensible materials. Such extensibility should enable both layers to be extended in the same direction. At least one of bodyside liner 24 and outer cover 26 preferably is resiliently extensible, i.e. retractable to substantially its original length or width upon release of the extending force. In such embodiments, at least one of bodyside liner 24 and outer cover 26 can return absorbent article 8 to substantially its original size and shape upon release of fastening tabs 20, 22 or other such restraints. In such an instance, the element that is merely extensible can follow the retractable liner/cover to the restorative size upon release. In other embodiments, both bodyside liner 24 and outer cover 26 can be resiliently extensible, and thus can and do assist each other in returning absorbent article 8 to its earlier relaxed size and shape upon release of fastening tabs 20, 22.

Leg elastics 28 may be formed from separate materials which are attached to outer cover 26 and/or bodyside liner 24. Materials suitable for forming the leg elastics include LYCRA® strands, ribbons, or one or more layers of a polymeric and/or elastomeric material that may be adhered to absorbent article 8, thus forming leg elastics 28, while in a stretched or extended position. Leg elastics 28 provide limited extensibility of the absorbent article in longitudinal direction "L", from and to a relaxed condition. Alternatively, the material forming leg elastic 28 can be attached, in a relaxed condition, to absorbent article 8 while the article is pleated, such that elastic constrictive forces are imparted to at least crotch portion 18 of absorbent article 8 when the leg elastic is elongated along the length of the absorbent article.

In the embodiment of FIG. 3, where outer cover 26 and/or bodyside liner 24 are formed from materials at least stretchable in longitudinal direction "L", extensible leg elastics 28 need not be provided for absorbent article 8.

Opposing left and right spaced containment flaps 30, 32 extend longitudinally along the length of absorbent article 8 inwardly of respective side edges 34, 36 of the absorbent article. In such embodiments as in FIG. 3, containment flaps 30, 32 are typically secured to bodyside liner 24. Dashed lines 56 indicate where the entire surface of the containment flaps which are facing bodyside liner 24 are secured to the bodyside liner outwardly from crotch portion 18. Inwardly from dashed lines 56, containment flaps 30, 32 are secured to bodyside liner 24 only at inward edges thereof, and thus can stand up or otherwise open to receive and restrain exudates.

Exemplary containment flaps are set forth in U.S. Pat. No. 4,704,116 issued Nov. 3. 1987 to K. Enloe, the disclosure of which is hereby incorporated by reference in its entirety to the extent that it is consistent (not contradictory) herewith.

Waist elastics (not shown) generally extend about the waist of absorbent article 8. Front waist elastics and rear waist elastics (not shown) generally comprise strands, ribbons or one or more layers of a polymeric and/or elastomeric material which can be adhered or otherwise mounted in absorbent article 8 while the elastic is in a stretched condition. Waist elastics can comprise one or more individual strands of elastomeric material, preferably in a spatially separated, generally parallel arrangement.

In some embodiments comprising extensible outer covers 26 and/or extensible bodyside liners 24, waist elastics can be omitted. Extensible bodyside liner 24 and extensible outer cover 26 can obviate the need for waist elastics while retaining the appropriate stretch function.

Absorbent pad 38 may be manufactured in a wide variety of sizes and shapes (for example, rectangular, trapezoidal, T-shape, I-shape, hourglass shape, etc.) and from a wide variety of materials. The size, and absorbent capacity, of absorbent pad 38 should be compatible with the size of the intended wearer and the anticipated liquid loading imparted by the intended use of the absorbent pad.

Absorbent pad 38 contains absorbent core 44 enveloped by barrier tissue 40 and forming tissue 42. Adhesive 46 preferably comprises cold adhesive applied to barrier tissue 40 and/or forming tissue 42 about at least the outer perimeter of absorbent core 44. Other known adhesives or bonding techniques may be utilized in place of cold adhesive to secure first surface 48 of barrier tissue 40 to first surface 52 of forming tissue 42.

Barrier tissue 40 typically comprises a single-ply, low porosity creped wadding or the like. Other tissues can also function as barrier tissue 40 provided the proper porosity and other characteristics are present. An exemplary barrier tissue has a basis weight of 12.5 pounds/ream (a ream comprising about 3000 square feet), a porosity of approximately 90 cubic feet per minute per foot squared, and dry strength of about 500 grams.

Forming tissue 42 typically comprises a material similar to barrier tissue. An exemplary forming tissue 42 has a porosity of approximately 400 cubic feet per minute per foot squared, and dry strength of about 730 grams. Other forming tissues made from materials having suitable characteristics may also be utilized.

In some absorbent article manufacturing processes, the forming tissue is disposed between absorbent core 44 and bodyside liner 24. In such processes, the barrier tissue is disposed between absorbent core 44 and outer cover 26. Therefore, in the claimed invention, the tissue disposed between absorbent core 44 and outer cover 26 can be considered a first tissue (comprising a forming tissue or a barrier tissue) and the tissue disposed between absorbent core 44 and bodyside liner 24 can be considered a second tissue (comprising a forming tissue or a barrier tissue).

Second surface 54 of forming tissue 42 defines a contact area in general surface-to-surface relationship with second inner surface 64 of outer cover 26. Release agent 70 acts as a coating distributed over substantially the entirety of. or a necessary portion of, the contact area on second surface 54 of forming tissue 42 which can potentially come into contact with adhesive layer 66 on second inner surface 64 of outer cover 26.

Absorbent core 44 suitably comprises a matrix of hydrophilic fibers, such as a web of cellulosic fluff, preferably in combination with a high-absorbency material commonly known as superabsorbent material. In a preferred embodiment, absorbent core 44 comprises a mixture of superabsorbent hydrogel-forming material and wood pulp fluff. In place of the wood pulp fluff, one may use synthetic, polymeric, meltblown fibers or a combination of meltblown fibers and natural fibers. The superabsorbent material may be substantially homogeneously mixed with the hydrophilic fibers or may be otherwise combined into the absorbent core.

Alternatively, absorbent core 44 may comprise a laminate of fibrous webs and superabsorbent material or other suitable means of maintaining a superabsorbent material in a localized area.

The high-absorbency material in absorbent core 44 can be selected from natural, synthetic and modified natural polymers and materials. The high absorbency materials can be inorganic materials, such as silica gels, or organic compounds, such as cross-linked polymers. The term cross-linked refers to any means for effectively rendering normally water-soluble materials substantially water insoluble but swellable, whereby absorbent properties are available but the swelled material is substantially immobile after absorbing water-based liquids. Such means can include, for example, physical entanglement, crystalline domains, covalent bonds, ionic complexes and associations, hydrophilic associations such as hydrogen bonding, and hydrophobic associations or Van der Waals forces.

Bodyside liner 24 is secured to outer cover 26 about at least an outer perimeter of absorbent pad 38. Typically, such securement is provided by adhesive 66. Adhesive 66 can comprise a full width adhesive applied to second surface 64 of outer cover 26 as shown in FIG. 2. Adhesive 66, however, can comprise a set of spaced lines of adhesive extending in longitudinal direction "L". Adhesive 66 preferably can comprise overlapping swirls of adhesive following the center distance between spray guns of spaced adhesive applicators (not shown) aligned across one direction of the product. Such an arrangement decreases the amount of adhesive required and maintains securement of second surface 64 of outer cover 26 to second surface 60 of bodyside liner 24.

In instances where bodyside liner 24 and outer cover 26 are extensible in both cross direction "C" and longitudinal direction "L", adhesive 66 can comprise other patterns not including solid lines of adhesive in the longitudinal direction. For example, adhesive 66 could comprise an angled pattern of adhesives or spaced unconnected areas of adhesive. Such patterns prevent or limit adhesive 66 from "locking up" stretch of outer cover 26 in longitudinal direction "L" or cross direction "C". As used herein, "locking up" means an adhesive or glue preventing an extensible material from extending the amount designed because of the adhesive creating a bond at at least a surface of the extensible material.

In any instance, any portion of adhesive layer 66 positioned in surface-to-surface relationship with forming tissue 42, thus to contact or adhere outer cover 26 to absorbent pad 38, except along a longitudinal centerline in some embodiments, must be prevented from contacting or adhering to the outer cover by release agent 70.

Release agent 70 comprises a material applied either to at least a portion of second outer surface 54 of forming tissue 42 or to at least a portion of second surface 64 of outer cover 26 either before or after application of adhesive 66 to the outer cover and thus over adhesive layer 66. Applying release agent 70 to outer cover 26 before application of adhesive layer 66 allows the operation release agent to be applied and dried on the outer cover prior to manufacturing absorbent article 8.

Although release agent 70 appears to be a relatively thick layer in FIG. 2, release agent 70 can be a relatively thin coating of material such that the material would not be visible to unaided visual observation in the cross section of FIG. 2. The cross-section of FIG. 2 is for purposes of illustration only. None of the dimensions shown in FIG. 2 are necessarily accurate for any of the elements illustrated therein.

In some embodiments, release agent 70 comprises a silicone-active agent. The silicone-active agent preferably comprises an amino functional silicone. The silicone-active agent can be sprayed or otherwise applied, preferably to second surface 54 of forming tissue 42 before placement of absorbent pad 38 into contact with adhesive 66 on outer cover 26. The silicone-active agent can be sprayed as a liquid slurry/emulsion including silicone, water, and other materials. There are many silicones that will function properly. However, a silicone having an active amino content generates superior results. One preferred silicone emulsion is known as Dow No. 2-8153 manufactured by Dow Corning Corp. of Midland, Mich. Dow No. 2-8153 emulsion contains 35 weight percent solids, and dries out after application onto absorbent article 8. The amino functional silicone allows the silicone to bond to forming tissue 42, preferably without migrating through the forming tissue to absorbent core 44 or to opposing surface 52 of the forming tissue. Thus the silicone release agent bonds to forming tissue 42, but functions to repel attachment between outer cover 26 and absorbent pad 38.

Another preferred silicon emulsion is known as Dow No. 7224 manufactured by Dow Corning Corp. of Midland, Mich. Dow No. 7224 emulsion contains 32% by weight solids, and operates in a similar manner to the 2-8153 emulsion described above.

Release agent 70 can also comprise an effective amount of a powder material, such as corn starch, applied to at least one of second outer surface 54 of forming tissue 42 and second inner surface 64 of outer cover 26. The powder material has properties preventing adhesion of outer cover 26 to at least a portion of second surface 54 of forming tissue 42. The powder material preferably comprises corn starch. Other materials that can also be utilized as release agent 70 include talc, talcum powder, certain baby powders, baking soda, superabsorbent material, calcium sterate, and erucamide. None of the materials listed above, migrate through forming tissue 42. Other products having similar properties may be utilized in place of the powder materials listed above.

Surge layer 72 generally is located between barrier tissue 40 and bodyside liner 24. Surge layer 72 assists in spread of exudates over a substantial portion of absorbent pad 38. Thus surge layer 72 assists absorbent pad 38 in absorbing a sudden large amount of urine or other body exudates. First surface 74 of surge layer 72 is in surface-to-surface contact with second surface 50 of barrier tissue 40 and second surface 76 of the surge layer is in surface-to-surface contact with second surface 60 of bodyside liner 24.

Surge layer 72 can comprise materials set forth in U.S. Pat. No. 5,486,166 issued Jan. 23, 1996 to C. Ellis and D. Bishop. entitled, "Fibrous Nonwoven Web Surge Layer for Personal Care Absorbent Articles and the Like"; and U.S. Pat. No. 5,490.846 issued Feb. 13, 1996 to C. Ellis and R. Everett, entitled, "Improved Surge Management Fibrous Nonwoven Web for Personal Care Absorbent Articles and the Like"; the disclosures of which are herein incorporated by reference to the extent the disclosures are consistent (not contradictory) with the information disclosed herein. Further, other surge layer materials known in the art can also be utilized.

Optionally, a line of adhesive (not shown) extending in the longitudinal direction "L" in a manner similar to line of adhesive 78 can be located between surge layer 72 and absorbent pad 38. Such a line of adhesive prevents absorbent pad 38 from shifting laterally a significant distance, while permitting bodyside liner 24 to extend, at least in the cross-direction "C", a desired distance. Such an arrangement ensures absorbent pad 38 remains centered in absorbent article 8.

In another embodiment of the invention, line of adhesive 78, and any adhesive disposed between disposed between surge layer 72 and absorbent pad 38, can be located at spaced intervals along longitudinal direction "L". For example, line of adhesive 78 can comprise a broke line of adhesive sections intermittently sprayed onto surge layer 72 or bodyside liner 24. Thus, for embodiments having bodyside liner 24 and outer cover 26 both extensible in cross-direction "C" and longitudinal direction "L", adhesive 78 will not significantly lock up, or prevent extension of the bodyside liner in the longitudinal direction. Any adhesive between surge layer 72 and absorbent pad 38 can be applied in a similar manner.

In a preferred manufacturing operation, release agent 70 is applied to second outer surface 54 of forming tissue 42. The release agent can be pre-applied to forming tissue 42 before starting the manufacturing process for absorbent article 8. Release agent 70 comprises a relatively thin coating of silicone or powder material at second outer surface 54. Pre-applying the silicone coating allows the silicone to dry onto forming tissue 42 before manufacturing of absorbent article 8. At a different location in the manufacturing process, adhesive 66 is applied to second inner surface 64 of outer cover 26. Adhesive 66 can cover (i) the entire surface of outer cover 26, (ii) conventional patterns, or (iii) the patterns described earlier herein. Upon completion of the above steps, absorbent pad 38 including forming tissue 42 is applied to outer cover 26 such that the release coated second outer surface 54 of the forming tissue is in surface-to-surface relationship with at least a portion of second inner surface 64 of the outer cover, such that the outer cover, including a portion of adhesive 66, interacts with release agent 70. Thus over the portion of forming tissue 42 where release agent 70 interacts with adhesive 66, the release agent prevents the adhesive from adhering at least a portion of outer cover 26 to absorbent pad 38. Therefore, resilient extension of outer cover 26 in at least cross-direction "C", without damage to absorbent pad 38, is enabled.

Hot melt adhesive 78 is applied to second surface 60 of bodyside liner 24, and surge layer 72 is applied thereto. Thus, second surface 76 of surge layer 72 is secured by the adhesive in surface-to-surface relationship with second surface 60 of bodyside liner 24.

Manufacturing absorbent article 8 can, of course, include applying bodyside liner 24 to second surface 50 of barrier tissue 40 such that the bodyside liner overlies, and extends outwardly of, absorbent pad 38. Thus bodyside liner 24 overlies and contacts portions of outer cover 26 that extend outwardly of absorbent pad 38 as illustrated in FIG. 2. Adhesive 66 thus secures outer perimeter of outer cover 26 to bodyside liner 24.

Manufacture of absorbent article 8 having release agent 70, applied as shown in FIG. 2, has no adhesion of absorbent pad 38 relative to bodyside liner 24 and outer cover 26. Thus, the embodiment of FIGS. 1 and 2 enables bodyside liner 24 and outer cover 26 to be extensible, preferably resiliently extensible. without applying strain during extension that could potentially break absorbent pad 38 and release superabsorbent material therefrom.

Those skilled in the art will now see that certain modifications can be made to the invention herein disclosed with respect to the illustrated embodiments, without departing from the spirit of the instant invention. And while the invention has been described above with respect to the preferred embodiments, it will be understood that the invention is adapted to numerous rearrangements, modifications, and alterations, all such arrangements. modifications, and alterations are intended to be within the scope of the appended claims.

To the extent the following claims use means plus function language, it is not meant to include there, or in the instant specification, anything not structurally equivalent to what is shown in the embodiments disclosed in the specification.

Having thus described the invention, what is claimed is:

1. An absorbent article including a rear portion, a front portion, and a crotch portion connecting said rear portion and said front portion, said absorbent article having a cross direction extending across the absorbent article and a longitudinal direction extending through the front, crotch, and rear portions, said absorbent article comprising:

(a) an absorbent pad having a first surface and an opposing second surface;

(b) an outer cover having a third outer cover surface and a fourth opposing outer cover surface;

(c) a pattern of adhesive material disposed on the first surface of said absorbent pad or on the third outer cover surface of said outer cover;

and (d) an effective amount of a release agent disposed on one of the first surface of said absorbent pad and at least a portion of the third surface of said outer cover, said release agent preventing adhesion of the third surface of said outer cover to the first surface of said absorbent pad such that said absorbent pad has substantially no adhesion over the surface effectively treated with said release agent with respect to said outer cover.

2. An absorbent article as in claim 1, said absorbent article including first and second containment flaps.

3. An absorbent article as in claim 1, said release agent comprising a silicone-active agent disposed on one of the first surface of said absorbent pad and the third surface of said outer cover.

4. An absorbent article as in claim 3, said silicone-active agent comprising an amino functional silicone.

5. An absorbent article as in claim 1, said release agent comprising a powder material applied to one of the first surface of said absorbent pad and the third surface of said outer cover.

6. An absorbent article as in claim 5, said powder material comprising corn starch.

7. An absorbent article as in claim 5, said powder material comprising erucamide.

8. An absorbent article as in claim 5, said powder material comprising baking soda.

9. An absorbent article as in claim 5, said powder material comprising superabsorbent material.

10. An absorbent article as in claim 5, said powder material comprising calcium sterate.

11. An absorbent article as in claim 1, said absorbent pad having an outer perimeter, said adhesive material securing said outer cover to said bodyside liner at locations disposed outwardly of the outer perimeter of said absorbent pad.

12. An absorbent article as in claim 1, said absorbent article being free from waist elastic elements.

13. An absorbent article as in claim 1, said absorbent article including leg elastics disposed at least in the crotch portion of said absorbent article, said leg elastics providing extensibility and retraction in the longitudinal direction.

14. An absorbent article as in claim 1, said absorbent pad including a first tissue having a fifth surface and an opposing sixth surface, the fifth surface of said first tissue being disposed in surface-to-surface relationship with the first surface of said absorbent core, the sixth surface of said first tissue being disposed in surface-to-surface relationship with the third outer cover surface, such that said release agent is applied to one of said first tissue of said absorbent pad and at least a portion of the third surface of said outer cover.

15. An absorbent article as in claim 14, including a bodyside liner, and including a second tissue disposed between said bodyside liner and said absorbent core.

16. An absorbent article as in claim 15, said absorbent article including a surge layer disposed between said bodyside liner and said second tissue.

17. An absorbent article as in claim 15, at least one of said bodyside liner and said outer cover comprising resiliently extensible material.

18. An absorbent article as in claim 17, said bodyside liner and said outer cover both being resiliently extensible, and having substantially the same amount of extensibility in a given direction.

19. An absorbent article as in claim 17, said bodyside liner and said outer cover both being extensible in at least the cross-direction.

20. An absorbent article as in claim 17, said outer cover comprising a necked bonded laminate.

21. An absorbent article as in claim 15, said second tissue and said first tissue being secured to each other about at least a portion of an outer perimeter of said absorbent core, said second tissue and said first tissue enclosing said absorbent core.

22. An absorbent article including a rear portion, a front portion, and a crotch portion connecting said rear portion and said front portion, said absorbent article having a cross direction extending across the absorbent article and a longitudinal direction extending through the front, crotch, and rear portions, said absorbent article comprising:

(a) an outer cover having a first inner surface and an opposing second outer surface;

(b) a bodyside liner having a third body contacting surface and an opposing fourth surface, the fourth surface of said bodyside liner being mounted in surface-to-surface relationship to at least a portion of the first inner surface of said outer cover;

(c) an absorbent pad located between said bodyside liner and said outer cover; said absorbent pad comprising an absorbent core having a first tissue disposed at a fifth surface of said absorbent pad adjacent said outer cover, and a second tissue disposed at a sixth surface of said absorbent pad adjacent said bodyside liner;

(d) adhesive material disposed on at least a portion of the first surface of said outer cover or on at least a portion of said first tissue; and (e) a release agent applied to at least one of said first tissue and said first surface of said outer cover;

said release agent interacting with said adhesive material and thereby preventing adhesion of said adhesive material to one of said outer cover and said first tissue.

23. An absorbent article as in claim 22, said outer cover comprising an extensible material, said release agent thus permitting extension of said outer cover in the cross-direction without damage to said absorbent pad.

24. An absorbent article as in claim 23, said outer cover comprising a necked bonded laminate.

25. An absorbent article as in claim 23, said bodyside liner comprising an extensible material.

26. An absorbent article as in claim 25, said bodyside liner and said outer cover both being extensible in at least the cross-direction, said release agent enabling said outer cover to extend at least about 30 percent in the cross-direction without damaging said absorbent pad.

27. An absorbent article as in claim 26, said release agent enabling said outer cover to extend at least about 200 percent in the cross-direction without damaging said absorbent pad.

28. An absorbent article as in claim 27, said release agent enabling said outer cover to extend at least about 30 percent in the longitudinal direction without damaging said absorbent pad.

29. An absorbent article as in claim 22, said absorbent article including a surge layer secured to at least said bodyside liner, said surge layer being disposed between said bodyside liner and said absorbent pad.

30. An absorbent article as in claim 22, said absorbent article including leg elastics disposed at least in the crotch portion of said absorbent article.

31. An absorbent article as in claim 22, said absorbent article including first and second containment flaps.

32. An absorbent article as in claim 22, said release agent comprising a silicone-active agent disposed on said first tissue prior to assembly of said absorbent article.

33. An absorbent article as in claim 32, said first tissue defining a contact area thereof in general surface-to-surface relationship with said first inner surface of said outer cover, said silicone-active agent acting as a coating distributed over substantially the entirety of the contact area of said first tissue.

34. An absorbent article as in claim 22, said release agent comprising powder material applied to one of said first tissue and the first surface of said outer cover.

35. An absorbent article as in claim 22, said first tissue having a seventh surface in surface-to-surface relationship with said absorbent core and an eighth opposing surface receiving said release agent.

36. An absorbent article as in claim 22, said first tissue and said second tissue being secured to each other about said absorbent core, such that said absorbent core is enclosed by the combination of said first tissue and said second tissue to thereby form said absorbent pad.

37. An absorbent article as in claim 22, said absorbent pad having an outer perimeter thereabout, said adhesive material securing said outer cover to said bodyside layer at locations disposed outwardly of the outer perimeter of said absorbent pad, said release agent preventing securement between said outer cover and said absorbent pad such that said absorbent pad has substantially no adhesion to said outer cover over the surface effectively treated with said release agent.

38. An absorbent article as in claim 22, said absorbent pad being unattached to either of said bodyside liner or said outer cover.

39. A method of making an absorbent article having extensibility in at least one direction, the method including the steps of:

(a) applying a release agent to a first outer surface of a first tissue, the first tissue, in combination with a second tissue substantially enclosing an absorbent core to thereby form an absorbent pad wherein the first outer surface of the first tissue, having the release agent thereon, corresponds with an outer surface of the absorbent pad;

(b) applying adhesive to a second inner surface of an extensible outer cover; and (c) placing at least a first portion of the first surface of the first tissue of the absorbent pad in surface-to-surface relationship with at least a second portion of the second surface of the outer cover such that the outer cover, including a portion of the adhesive, interacts with the release agent;

whereby over that portion of the first tissue wherein the release agent interacts with the adhesive, the release agent prevents the adhesive from adhering the outer cover to the absorbent pad, and thus permits resilient extension of the outer cover in at least one direction without damage to the absorbent pad.

40. A method as in claim 39, the second tissue having a third surface on a side of the absorbent pad opposing the first surface of the first tissue, the method including the step of applying a bodyside liner to the third surface of the second tissue such that the bodyside liner overlies, and extends outwardly of, the absorbent pad, and overlies and contacts portions of the outer cover which extend outwardly of the absorbent pad, including the bodyside liner contacting at least part of the adhesive on the outer cover which is disposed outwardly from an outer perimeter of the absorbent pad.

41. A method as in claim 40, the method including applying a longitudinally-extending line of hot melt adhesive to a first surface of a surge layer, and adhesively securing the surge layer to the bodyside liner such that the surge layer is located between the bodyside liner and the absorbent pad.

42. A method as in claim 39, the method including applying cold adhesive to secure the first tissue to the second tissue about substantially an entire perimeter of facing portions of the first tissue and the second tissue such that the combination of the first tissue and the second tissue provides a closed enclosure within which the absorbent core is received.

43. A method as in claim 39, the adhesive applied to the outer cover comprising a hot melt adhesive sprayed onto the second surface.

44. A method as in claim 39, the applying of the release agent comprising applying, onto one of the first surface of the first tissue, and the second surface of the outer cover, an amount of silicone-active agent effective to prevent the adhesive on the outer cover from adhering to the first tissue.

45. A method as in claim 39, the applying of the release agent comprising applying, onto at least one of the first surface of the first tissue and the second of the outer cover, an amount of powder material effective to prevent the adhesive on the outer cover from adhering to the first tissue.

46. A method as in claim 45, the powder material comprising corn starch.

47. An absorbent article as in claim 45, said powder material comprising erucamide.

48. An absorbent article as in claim 45, said powder material comprising calcium sterate.

49. An absorbent article as in claim 39, the release agent being pre-applied to the first tissue before starting the manufacturing process for the absorbent article.

* * * * *

UNITED STATES PATENT AND TRADEMARK OFFICE
CERTIFICATE OF CORRECTION

PATENT NO.   : 6,020,535
DATED          : February 1, 2000
INVENTOR(S) : Timothy J. Blenke et al.

It is certified that error appears in the above-identified patent and that said Letters Patent is hereby corrected as shown below:

Column 5,
Line 9, delete "48" and insert -- 52 -- in place thereof.

Column 12,
Line 25, delete the second occurrence of the words "disposed between".

Claim 45,
Line 3, after "second" insert -- surface --.

Signed and Sealed this

Twentieth Day of November, 2001

Attest:

NICHOLAS P. GODICI
*Attesting Officer*   *Acting Director of the United States Patent and Trademark Office*